United States Patent
Henderson et al.

(10) Patent No.: US 9,861,766 B2
(45) Date of Patent: Jan. 9, 2018

(54) MEDICAMENT DELIVERY DEVICE WITH NEEDLE ALIGNMENT DETECTION MECHANISM

(71) Applicant: SANOFI-AVENTIS DEUTSCHLAND GMBH, Frankfurt am Main (DE)

(72) Inventors: Charley Henderson, Cambridgeshire (GB); David Cross, Hertfordshire (GB); Douglas Ivan Jennings, Hertfordshire (GB); Ryan Anthony McGinley, Cambridgeshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 228 days.

(21) Appl. No.: 14/426,780

(22) PCT Filed: Sep. 10, 2013

(86) PCT No.: PCT/EP2013/068714
§ 371 (c)(1),
(2) Date: Mar. 9, 2015

(87) PCT Pub. No.: WO2014/040985
PCT Pub. Date: Mar. 20, 2014

(65) Prior Publication Data
US 2015/0238708 A1    Aug. 27, 2015

(30) Foreign Application Priority Data
Sep. 11, 2012    (EP) ..................... 12183929

(51) Int. Cl.
*A61M 5/32*    (2006.01)
*A61M 5/50*    (2006.01)

(52) U.S. Cl.
CPC ........ *A61M 5/5086* (2013.01); *A61M 5/3287* (2013.01); *A61M 2205/6027* (2013.01); *A61M 2205/70* (2013.01)

(58) Field of Classification Search
CPC .......... A61M 5/158; A61M 2005/1585; A61M 5/24; A61M 2005/3249; A61M 25/0618;
(Continued)

(56) References Cited

U.S. PATENT DOCUMENTS 5,598,269 A * 1/1997 Kitaevich ............... A61B 6/08
356/399
6,572,526 B1    6/2003 Ford
(Continued)

FOREIGN PATENT DOCUMENTS

| FR | 2867083 | 9/2005 |
| WO | 2009/142878 | 11/2009 |
| WO | 2011/101377 | 8/2011 |

OTHER PUBLICATIONS

International Search Report for Int. App. No. PCT/EP2013/068714, completed Sep. 25, 2013.

*Primary Examiner* — Gerald Landry, II
(74) *Attorney, Agent, or Firm* — Fish & Richardson P.C.

(57) ABSTRACT

Described is a medicament delivery device comprising a case, a container slidably disposed in the case between a first position and a second position, a needle coupled to the container, and a needle alignment detection mechanism disposed on the case and adapted to receive the needle. The needle alignment detection mechanism determines whether the needle is aligned with a longitudinal axis (L) when the needle is in the first position, the second position or translating between the first position and the second position.

24 Claims, 5 Drawing Sheets

(58) Field of Classification Search
CPC .. A61M 5/1626; A61M 5/3287; A61M 5/322; A61M 5/34; A61M 5/5086; A61M 2205/6207; A61M 2205/70
USPC .......................... 604/67, 111, 198, 263, 533
See application file for complete search history.

(56) References Cited

U.S. PATENT DOCUMENTS

| | | | |
|---|---|---|---|
| 6,846,282 B1 | 1/2005 | Ford | |
| 2001/0053915 A1* | 12/2001 | Grossman | A61B 90/13 606/130 |
| 2002/0052618 A1* | 5/2002 | Haar | A61B 5/15146 606/181 |
| 2002/0198483 A1* | 12/2002 | Wariar | A61M 5/158 604/5.01 |
| 2003/0139700 A1* | 7/2003 | Elliott | A61N 5/1007 604/62 |
| 2004/0092889 A1* | 5/2004 | Ferguson | A61M 25/0618 604/263 |
| 2005/0159709 A1* | 7/2005 | Wilkinson | A61M 5/326 604/197 |
| 2005/0197650 A1* | 9/2005 | Sugimoto | A61M 5/20 604/890.1 |
| 2007/0030017 A1* | 2/2007 | Choi | G01R 1/06794 324/750.24 |
| 2007/0106231 A1* | 5/2007 | Snow | A61M 5/3273 604/263 |
| 2008/0294143 A1* | 11/2008 | Tanaka | A61B 1/041 604/506 |
| 2009/0082782 A1* | 3/2009 | Kalpin | A61B 17/3403 606/130 |
| 2009/0275823 A1* | 11/2009 | Ayati | A61B 5/489 600/424 |
| 2010/0021348 A1* | 1/2010 | Baldassari | G06T 1/0014 422/400 |
| 2010/0106015 A1* | 4/2010 | Norris | A61B 10/0275 600/437 |
| 2010/0137695 A1* | 6/2010 | Yodfat | A61B 5/6849 600/345 |
| 2010/0217105 A1* | 8/2010 | Yodfat | A61B 5/14503 600/365 |
| 2010/0247513 A1* | 9/2010 | Agee | A61B 17/320036 424/94.67 |
| 2010/0298705 A1* | 11/2010 | Pelissier | A61B 8/0833 600/443 |
| 2011/0066131 A1* | 3/2011 | Cabiri | A61M 5/14248 604/411 |
| 2011/0112549 A1* | 5/2011 | Neubach | A61B 8/485 606/130 |
| 2011/0160655 A1* | 6/2011 | Hanson | A61M 5/1413 604/67 |
| 2011/0178472 A1* | 7/2011 | Cabiri | A61M 5/14248 604/198 |
| 2011/0266149 A1* | 11/2011 | Say | A61B 5/1411 204/403.01 |
| 2011/0270061 A1* | 11/2011 | Say | A61B 5/1411 600/345 |
| 2011/0301629 A1* | 12/2011 | Manabe | A61B 5/0002 606/182 |
| 2012/0165747 A1* | 6/2012 | Lanin | A61M 5/14244 604/207 |
| 2012/0215163 A1* | 8/2012 | Hanson | A61M 5/1413 604/67 |
| 2013/0172819 A1* | 7/2013 | Iio | A61M 5/20 604/111 |
| 2014/0188075 A1* | 7/2014 | Eggert | A61M 5/20 604/506 |

* cited by examiner

MEDICAMENT DELIVERY DEVICE WITH NEEDLE ALIGNMENT DETECTION MECHANISM

CROSS REFERENCE TO RELATED APPLICATIONS

The present application is a U.S. National Phase Application pursuant to 35 U.S.C. §371 of International Application No. PCT/EP2013/068714 filed Sep. 10, 2013, which claims priority to European Patent Application No. 12183929.4 filed Sep. 11, 2012. The entire disclosure contents of these applications are herewith incorporated by reference into the present application.

TECHNICAL FIELD

The invention relates to a medicament delivery device with a needle alignment detection mechanism.

BACKGROUND

Conventional medicament delivery devices, e.g., pen injectors, autoinjectors, syringes, etc., typically utilize a syringe or cartridge containing a medicament, and the syringe or cartridge has an integral needle or removable needle assembly. The conventional medicament delivery devices typically do not check needle alignment prior to an injection. The needle can be bent prior to the injection when, for example, there is a manufacturing defect, there is bending during shipping, when a cap or needle boot is placed on the device during manufacture, when the cap or the needle boot is being removed prior to use, or during handling of the device prior to or during use.

A bent needle can be problematic for several reasons. For example, a bent needle may affect dosing (e.g., if a flow path for the medicament is disrupted). The bent needle may alter an intended injection depth. The bent needle may lead to a more painful injection due to a non-perpendicular insertion of the needle.

Thus, there remains a need for an improved medicament delivery device with a needle alignment detection mechanism.

SUMMARY

It is an object of the present invention to provide an improved medicament delivery device with a needle alignment detection mechanism.

In an exemplary embodiment, a medicament delivery device according to the present invention comprises a case, a container slidably disposed in the case between a first position and a second position, a needle coupled to the container, and a needle alignment detection mechanism disposed on the case and adapted to receive the needle. The needle alignment detection mechanism determines whether the needle is aligned with a longitudinal axis when the needle is in the first position, the second position or translating between the first position and the second position.

In an exemplary embodiment, the container is a syringe or a cartridge.

In an exemplary embodiment, the needle is integrally formed with the container or removably coupled to the container.

In an exemplary embodiment, the needle alignment detection mechanism includes at least one hinged door disposed along a transverse axis. The door has a non-deflected position aligned with the transverse axis and a deflected position at an angle to the transverse axis. The at least one door is biased in the non-deflected position. The at least one door includes a first door and a second door, and the first door includes a first cut-out and the second door includes a second cut-out. When the doors are in the non-deflected positions, the cut-outs form a hole. The hole has a cross-section at least as large as a diameter of the needle. The cross-section includes a buffer space.

In an exemplary embodiment, the medicament delivery device further includes an interlock mechanism adapted to control a component in the delivery device. Transition of at least one of the doors to the deflected position causes activation of the interlock mechanism. The needle alignment detection mechanism includes at least one sensor adapted to detect a transition of at least one of the doors from the non-deflected position to the deflected position.

In an exemplary embodiment, the needle alignment detection mechanism includes an electrode coupled to the needle and a conductive transverse element having a hole adapted to receive the needle. Impingement of the needle on the transverse element creates a circuit.

In an exemplary embodiment, the needle alignment detection mechanism includes an electrode adjacent to the needle and a conductive transverse element having a hole adapted to receive the needle. Impingement of the needle on the transverse element results in a measured impedance change.

In an exemplary embodiment, the needle alignment detection mechanism includes two light sources disposed perpendicularly on a transverse element and two optical sensors each adapted to receive a respective optical signal from a given one of the light sources. Impingement of the needle on a center point of an intersection of light beams from the light sources generates a changed optical signal. Impingement of the needle on an intersection of light beams from the light sources other than a center point of the intersection generates a changed optical signal.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
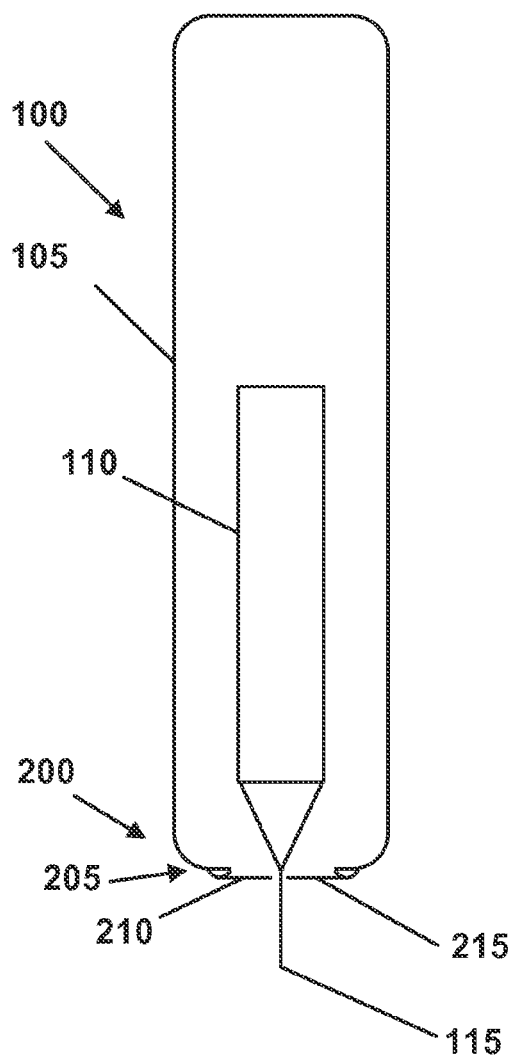
FIG. 1A-B shows an exemplary embodiment of a medicament delivery device with a needle alignment detection mechanism according to the present invention.
Figure 1B:
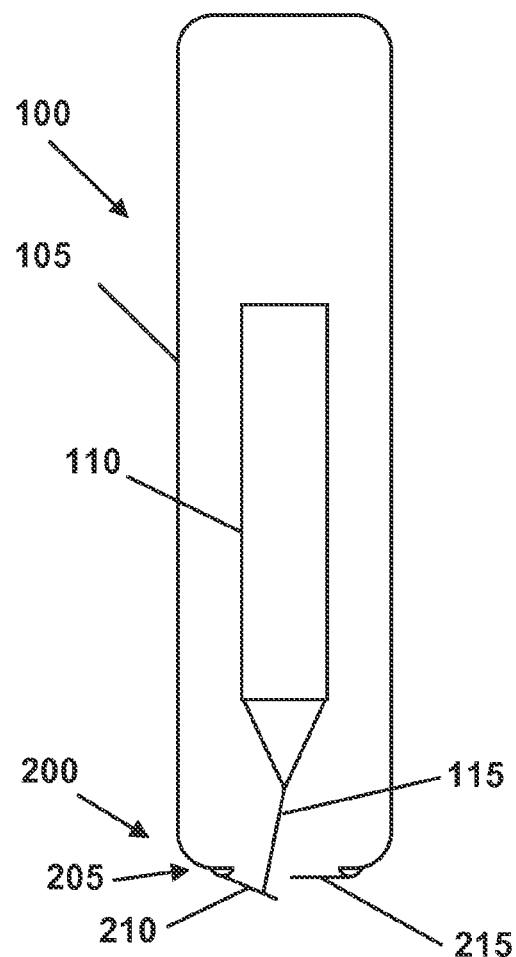

FIGS. 1A and 1B show an exemplary embodiment of a medicament delivery device 100 with a needle alignment detection mechanism 200 according to the present invention. The delivery device 100 may be any type of injection device which is used to inject a medicament from a syringe or cartridge. Those of skill in the art will understand that such injection devices include, but are not limited to, pen injectors, pre-filled syringes, autoinjectors, perfusion devices, infusion devices, etc.

In an exemplary embodiment, the needle alignment detection mechanism 200 is integrally formed with the delivery device 100. In another exemplary embodiment, the needle alignment detection mechanism 200 may be an attachment to a pre-existing delivery device. For example, the needle alignment detection mechanism 200 may be a cap-type attachment which is removably coupled to the delivery device 100 and can be reused.

In the exemplary embodiment, the delivery device 100 may include components common to conventional delivery devices such as, for example, a case 105, one or more springs, plungers, needle shields, a syringe 110 or a cartridge having an integral or removable needle 115 attached thereto, syringe/cartridge carriers, trigger button, etc.

In the exemplary embodiment, a needle alignment detection mechanism 200 is disposed on a distal end of the delivery device 100. The needle alignment detection mechanism 200 may detect an alignment of the needle 115 when the needle 115 has been deflected away from a longitudinal axis L, e.g., of the syringe 110 and/or the delivery device 100.

In an exemplary embodiment, the needle alignment detection mechanism 200 includes at least one cover element 205. The cover element 205 may be disposed distal of the needle 115 (assuming the syringe 110 moves distally for insertion of the needle 115 during an injection) such that during the injection, the needle 115 moves relative to the cover element 205.

In the exemplary embodiment shown in FIG. 1, the cover element 205 includes a first door 210 and a second door 215 disposed along a transverse axis T which is substantially perpendicular to the longitudinal axis L. The doors 210, 215 are hingedly disposed on the delivery device 100, and the non-deflected position corresponds to disposition along the transverse axis T. In an exemplary embodiment, a resilient element (e.g., a spring) may bias each door 210, 215 in the non-deflected position.

Figure 1C:
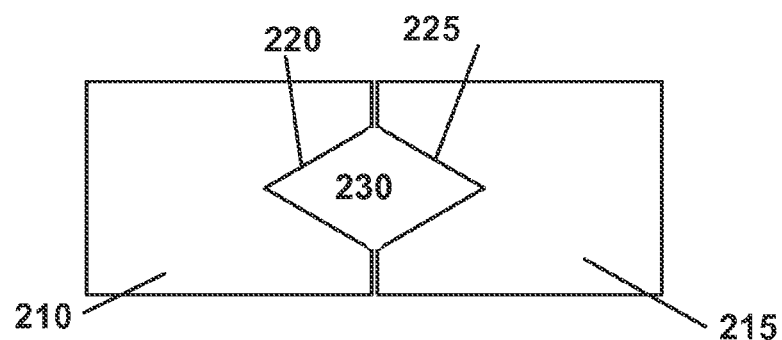
FIG. 1C shows an exemplary embodiment of the needle alignment detection mechanism of FIGS. 1A-B.

FIG. 1C shows an exemplary embodiment of the doors 210, 215 in the non-deflected position. Each door 210, 215 includes a cut-out 220, 225 such that, in the non-deflected position, the cut-outs abut and/or overlap to form a hole 230 through which a straight needle may pass. Thus, a diameter or cross-section of the hole 230 may correspond to a diameter of the needle 115 in addition to a surrounding buffer space for which the needle 115 will not be considered bent though it is not precisely aligned with the longitudinal axis L. The buffer space may provide some tolerance for needle/syringe manufacturing variability.

Referring back to FIGS. 1A and 1B, FIG. 1A shows an exemplary embodiment of the needle alignment detection mechanism 200 when a straight needle 115 passes through the hole 230. FIG. 1B shows an exemplary embodiment of the needle alignment detection mechanism 200 when a bent needle 115 abuts the first door 210. For example, the syringe 110 may be in a retracted position within the case 105 prior to use, and when the delivery device 100 is actuated, the syringe 110 may translate axially to insert the needle 115 into the injection site. If the needle 115 is bent, it may impact one of the doors 210, 215 and cause the impacted door to transition to the deflected position.

In an exemplary embodiment, an interlock mechanism may be activated when one of the doors 210, 215 transitions to the deflected position. The interlock mechanism may, for example, prevent further translation of the syringe 110 relative to the case 105, prevent translation of a plunger, activate a syringe refraction mechanism, activate a safety feature (e.g., deploy a needle shield), provide feedback (e.g., audible, visual, tactile to indicate bent needle), etc. In an exemplary embodiment, sensors for the needle alignment detection mechanism 200 may generate a signal when one of the doors 210, 215 transitions to the deflected position, and a controller in the delivery device 100 may activate the interlock mechanism.

In an exemplary embodiment, the sensors are electrodes disposed adjacent the doors 210, 215 which are made from or covered with a conducting material. If the one or both of the doors 210, 215 transition to the deflected position, a distance between the electrodes and the doors 210, 215 increase, a capacitance value between the electrodes changes, resulting in a change in measured impedance (or conductance). A change in the measured impedance may be used by a controller to activate the interlock mechanism.

In another exemplary embodiment, the sensors are optical sensors that include a reflectance-based proximity switch or photo-interrupter-based sensor actuated by the doors 210, 215 blocking a light beam focused on the sensor.

In another exemplary embodiment, the sensors measure current supplied to a motor in the delivery device 100 that drives the syringe 110 relative to the case 105. If the current is increased beyond a predetermined value (e.g., because the needle 115 impacts the doors 210, 215 and the motor must apply more force), the controller may activate the interlock mechanism.

In a further exemplary embodiment, the sensors may detect contact of the needle 115 with the doors 210, 215 which are locked in the non-deflected position.

Figure 2:
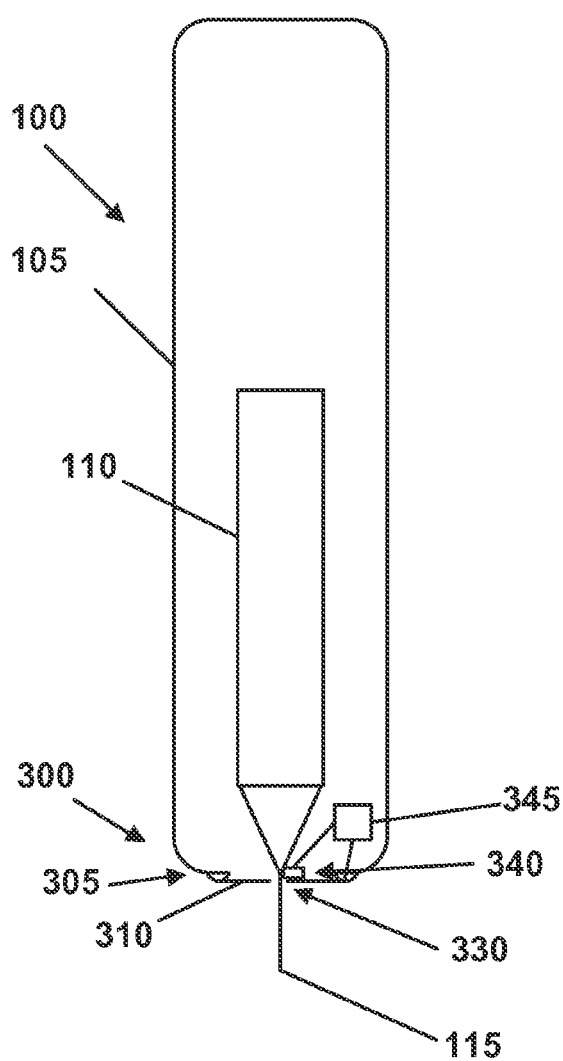
FIG. 2 shows another exemplary embodiment of a medicament delivery device with a needle alignment detection mechanism according to the present invention.

FIG. 2 shows another exemplary embodiment of a needle alignment detection mechanism 300 in which a cover element 305 includes a transverse element 310 including a hole 330 for allowing a straight needle to pass through. Thus, a diameter or cross-section of the hole 230 may correspond to a diameter of the needle 115 in addition to a surrounding buffer space for which the needle 115 will not be considered bent though it is not precisely aligned with the longitudinal axis L. The buffer space may provide some tolerance for needle/syringe manufacturing variability.

In this exemplary embodiment, an electrode 340 is coupled to the needle 115, e.g., at a proximal-most position, and the transverse element 310 is made or covered with a conductive metal. If the needle 115 is bent and impinges upon the transverse element 310, a circuit is created, and a controller 345 may activate an interlock mechanism.

Figure 3:
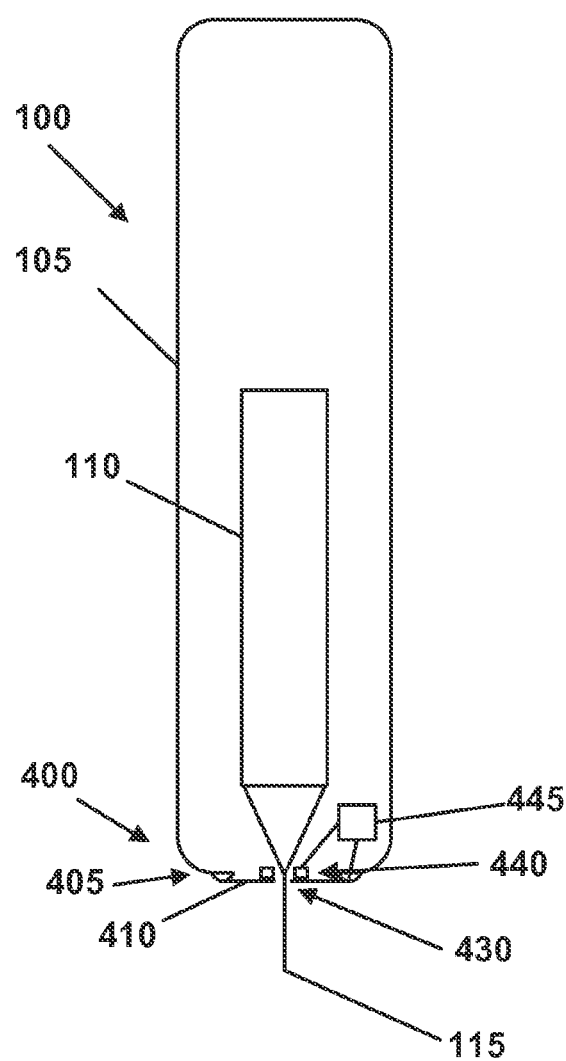
FIG. 3 shows another exemplary embodiment of a medicament delivery device with a needle alignment detection mechanism according to the present invention.

FIG. 3 shows another exemplary embodiment of a needle alignment detection mechanism 400 in which a cover element 405 includes a transverse element 410 including a hole 430 for allowing a straight needle to pass through. Thus, a diameter or cross-section of the hole 430 may correspond to a diameter of the needle 115 in addition to a surrounding buffer space for which the needle 115 will not be considered bent though it is not precisely aligned with the longitudinal axis L. The buffer space may provide some tolerance for needle/syringe manufacturing variability.

In this exemplary embodiment, an electrode 440 is disposed adjacent to the needle 115, e.g., at a proximal-most position, and the transverse element 410 is made or covered with a conductive metal. In this exemplary embodiment, the electrode 440 is a conductive cylinder surrounding, but not making physical contact with, a portion of the needle 115. While a cylinder is described in the exemplary embodiment, those of skill in the art will understand that the electrode 440 may overlap a surface of the needle 115. If the needle 115 is bent and impinges upon the transverse element 410, an impedance measurement will decrease due to change in overall capacitance between the electrode 440 and the transverse element 410, and a controller 445 may activate an interlock mechanism.

In another exemplary embodiment, the controller 445 may measure capacitance around the hole 430 and not utilize the electrode 440. If the needle 115 is bent and impinges upon the transverse element 410, the capacitance will change, and the controller 445 may activate an interlock mechanism.

Figure 4:
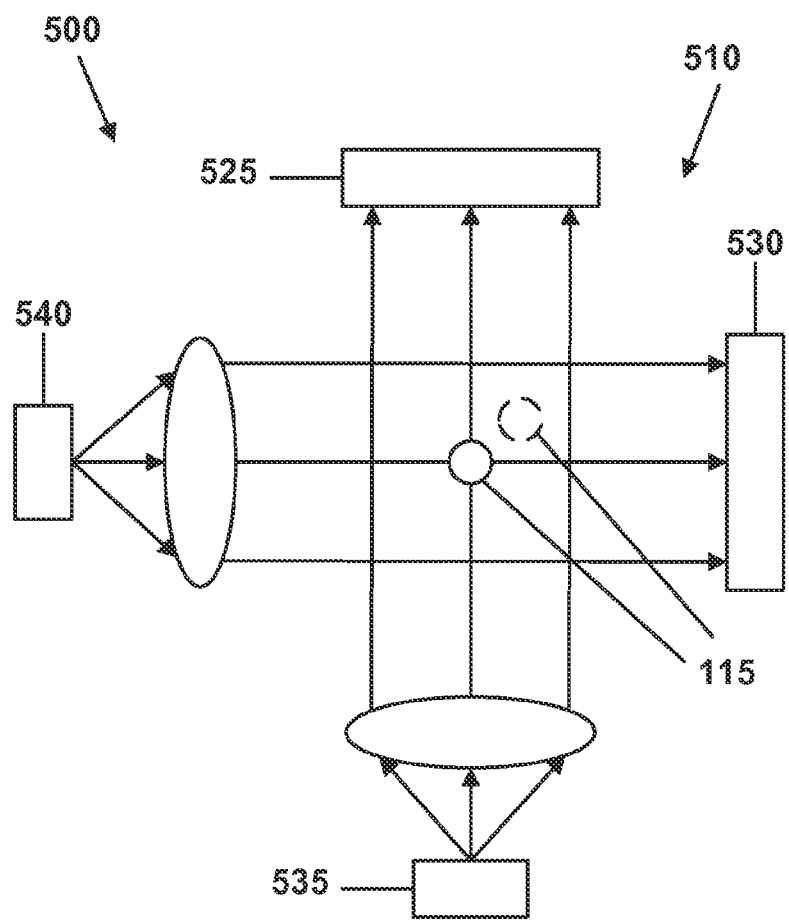
FIG. 4 shows another exemplary embodiment of a medicament delivery device with a needle alignment detection mechanism according to the present invention.

FIG. 4 shows another exemplary embodiment of a needle alignment detection mechanism 500 in which a cover element includes a transverse element 510 including a plurality of optical sensors. In the exemplary embodiment, two optical sensors 525, 530 are disposed perpendicularly on the transverse element 510 and receive optical signals from respective light sources 535, 540. Light beams from the light sources 535, 540 may intersect at a center point, which may have a diameter or cross-section corresponding to a diameter of the needle 115 in addition to a surrounding buffer space for which the needle 115 will not be considered bent though it is not precisely aligned with the longitudinal axis L. The buffer space may provide some tolerance for needle/syringe manufacturing variability. One or more lenses may be utilized to focus/spread the light beams to expand/limit a size of the center point. In an exemplary embodiment, if the needle 115 is not bent, then it will pass through the light beam (s) and reduce intensity of the light incidence on the sensor from its respective source. If the needle 115 is bent and does not pass through the center point, a controller may activate an interlock mechanism. Those of skill in the art will understand that in another exemplary embodiment, the light beams may be arranged to surround the center point such that if the needle is bent and pass through the light beams (and not the center point), the controller may activate the interlock mechanism.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament delivery device, comprising:
   a case;
   a container slidably disposed in the case between a first position and a second position;
   a needle coupled to the container; and
   a needle alignment detection mechanism disposed on the case and adapted to receive the needle,
   wherein the needle alignment detection mechanism is configured to detect that the needle is bent relative to a longitudinal axis of the container when the container is in the first position, the second position, or translating between the first position and the second position.

2. The medicament delivery device according to claim 1, wherein the container is a syringe or a cartridge.

3. The medicament delivery device according to claim 1, wherein the needle is integrally formed with the container or removably coupled to the container.

4. The medicament delivery device according to claim 1, wherein the needle alignment detection mechanism includes at least one hinged door disposed along a transverse axis, wherein the at least one hinged door has a non-deflected position aligned with the transverse axis and a deflected position at an angle to the transverse axis.

5. The medicament delivery device according to claim 4, wherein the at least one hinged door is biased in the non-deflected position.

6. The medicament delivery device according to claim 4, wherein:

the at least one hinged door includes a first door and a second door each having a non-deflected position, the first door includes a first cut-out and the second door includes a second cut-out, and
   the first and second cut-outs are configured to form a hole when the first and second doors are in non-deflected positions.

7. The medicament delivery device according to claim 6, wherein the hole has a cross-section at least as large as a diameter of the needle.

8. The medicament delivery device according to claim 7, wherein the cross-section includes a buffer space.

9. The medicament delivery device according to claim 4, further comprising:
   an interlock mechanism adapted to control a component in the medicament delivery device,
   wherein at least one of the at least hinged one door is configured to, upon transitioning to the deflected position, activate the interlock mechanism.

10. The medicament delivery device according to claim 9, wherein the needle alignment detection mechanism includes at least one sensor adapted to detect a transition of at least one of the at least one hinged door from the non-deflected position to the deflected position.

11. The medicament delivery device according to claim 1, wherein the needle alignment detection mechanism includes an electrode coupled to the needle and a conductive transverse element having a hole adapted to receive the needle, wherein the needle is configured to impinge on the transverse element to create a circuit.

12. The medicament delivery device according to claim 1, wherein the needle alignment detection mechanism includes an electrode adjacent to the needle and a conductive transverse element having a hole adapted to receive the needle, wherein the needle is configured to impinge on the transverse element to cause a measurable impedance change.

13. The medicament delivery device according to claim 1, wherein the needle alignment detection mechanism includes
   two light sources disposed perpendicularly relative to one another on a transverse element, and
   two optical sensors each adapted to receive a respective optical signal from a given one of the two light sources.

14. The medicament delivery device according to claim 13, wherein the needle is configured to impinge on a center point of an intersection of light beams from the two light sources such that a changed optical signal is generated.

15. The medicament delivery device according to claim 13, wherein the needle is configured to impinge on an intersection of light beams from the two light sources other than a center point of the intersection such that a changed optical signal is generated.

16. The medicament delivery device according to claim 1, further comprising an interlock sleeve configured to provide feedback indicative of misalignment between the needle and the longitudinal axis when the needle alignment detection mechanism detects the misalignment.

17. The medicament delivery device according to claim 9, wherein the component is a syringe or a plunger, and the interlock mechanism is configured to, upon activation, inhibit translation of the syringe or the plunger relative to the case.

18. The medicament delivery device according to claim 11, further comprising an interlock mechanism configured to inhibit translation of a syringe or a plunger relative to the case when the circuit is created.

19. The medicament delivery device according to claim 12, further comprising an interlock mechanism configured to inhibit translation of a syringe or a plunger relative to the case upon detection of the measurable impedance change.

20. The medicament delivery device according to claim 1, wherein the needle is integrally formed with the container.

21. The medicament delivery device according to claim 1, wherein the needle extends distally from the container.

22. The medicament delivery device according to claim 1, wherein the first position corresponds to a retracted position in which the needle is retracted within the case, and the second position corresponds to an extended position in which the needle is insertable into an injection site.

23. The medicament delivery device according to claim 1, further comprising:
   an interlock mechanism configured to be activated to inhibit movement of at least a portion of the container or the needle, and
   a controller configured to activate the interlock mechanism in response to detecting that the needle is bent.

24. The medicament delivery device according to claim 1, wherein:
   the needle alignment detection mechanism comprises a sensor configured to generate a signal indicative of the needle being bent, and
   the medicament delivery device comprises a controller configured to activate an interlock mechanism in response to the signal.

* * * * *